(12) United States Patent
Reiner

(10) Patent No.: US 8,081,165 B2
(45) Date of Patent: Dec. 20, 2011

(54) MULTI-FUNCTIONAL NAVIGATIONAL DEVICE AND METHOD

(75) Inventor: Bruce Reiner, Seaford, DE (US)

(73) Assignee: JesterRad, Inc., Seaford, DE (US)

( * ) Notice: Subject to any disclaimer, the term of this patent is extended or adjusted under 35 U.S.C. 154(b) by 744 days.

(21) Appl. No.: 11/512,199

(22) Filed: Aug. 30, 2006

(65) Prior Publication Data

US 2007/0046649 A1 Mar. 1, 2007

Related U.S. Application Data

(60) Provisional application No. 60/712,134, filed on Aug. 30, 2005, provisional application No. 60/809,823, filed on Jun. 1, 2006.

(51) Int. Cl.
*G09G 5/00* (2006.01)

(52) U.S. Cl. ............... 345/173; 345/156; 178/19.01; 178/19.02

(58) Field of Classification Search ............. 345/173, 345/156; 178/19.01–19.02
See application file for complete search history.

(56) References Cited

U.S. PATENT DOCUMENTS

| | | | | |
|---|---|---|---|---|
| 4,221,404 | A * | 9/1980 | Shuffstall | 283/115 |
| 5,615,284 | A | 3/1997 | Rhyne et al. | |
| 5,867,821 | A | 2/1999 | Ballantyne et al. | |
| 6,173,068 | B1 | 1/2001 | Prokoski | |
| 6,266,595 | B1 | 7/2001 | Greatline et al. | |
| 6,375,622 | B1 * | 4/2002 | Kao et al. | 600/485 |
| 6,440,072 | B1 | 8/2002 | Schuman et al. | |
| 6,708,049 | B1 * | 3/2004 | Berson et al. | 600/323 |
| 6,711,547 | B1 | 3/2004 | Glover | |
| 6,886,061 | B2 * | 4/2005 | Yokota et al. | 710/73 |
| 6,901,277 | B2 | 5/2005 | Kaufman et al. | |
| 6,919,927 | B1 * | 7/2005 | Hyodo | 348/333.02 |
| 2001/0039502 | A1 | 11/2001 | Case | |
| 2002/0026331 | A1 | 2/2002 | Case | |
| 2002/0077841 | A1 | 6/2002 | Thompson | |
| 2002/0150302 | A1 | 10/2002 | McCarthy et al. | |
| 2003/0144874 | A1 | 7/2003 | Barret et al. | |
| 2003/0171791 | A1 * | 9/2003 | KenKnight et al. | 607/60 |
| 2003/0179223 | A1 | 9/2003 | Ying et al. | |
| 2004/0044894 | A1 * | 3/2004 | Lofgren et al. | 713/176 |
| 2004/0078215 | A1 | 4/2004 | Dahlin et al. | |

(Continued)

FOREIGN PATENT DOCUMENTS

DE 32 31 411 A1 3/1984

(Continued)

*Primary Examiner* — Richard Hjerpe
*Assistant Examiner* — Leonid Shapiro
(74) *Attorney, Agent, or Firm* — Jean C. Edwards, Esq.; Edwards Neils PLLC

(57) ABSTRACT

The present invention is related to a computer-implemented method of identifying and annotating an image from an electronic medical record displayed on a touch screen, which includes displaying the image on the touch screen; identifying medical issues shown in the image; annotating the image with at least one symbol correlated to predetermined information using a navigational device; and prioritizing the medical issues using the navigational device. The prioritizing step may include color-coding at least one of the symbol and the image using the navigational device. Further, the navigational device may include a pressure detecting mechanism which determines at least one of a priority of the image and a speed of images displayed on the touch screen, based on an amount of pressure exerted by a user on the touch screen. The navigational device includes security features to ensure authorized use, including biometric authentication of identification.

42 Claims, 4 Drawing Sheets

U.S. PATENT DOCUMENTS

| | | | |
|---|---|---|---|
| 2004/0167989 A1* | 8/2004 | Kline et al. | 709/245 |
| 2004/0260470 A1 | 12/2004 | Rast | |
| 2005/0015270 A1* | 1/2005 | Kato et al. | 705/1 |
| 2005/0065822 A1 | 3/2005 | Ying et al. | |
| 2005/0144038 A1* | 6/2005 | Tamblyn et al. | 705/2 |
| 2005/0216314 A1* | 9/2005 | Secor | 705/3 |
| 2005/0231488 A1* | 10/2005 | Chou | 345/179 |
| 2006/0061595 A1 | 3/2006 | Goede et al. | |
| 2006/0087497 A1* | 4/2006 | Borgaonkar et al. | 345/179 |
| 2007/0162301 A1* | 7/2007 | Sussman et al. | 705/1 |

FOREIGN PATENT DOCUMENTS

| | | |
|---|---|---|
| JP | 2000-325314 | 11/2000 |
| JP | 2003-271745 | 9/2003 |
| JP | 2004-213678 | 7/2004 |
| JP | 2005-202482 | 7/2005 |
| JP | 2005-202483 | 7/2005 |
| JP | 2005-202484 | 7/2005 |
| WO | WO 98/13783 | 4/1998 |
| WO | WO 03/096321 | 11/2003 |

* cited by examiner

MULTI-FUNCTIONAL NAVIGATIONAL DEVICE AND METHOD

CROSS-REFERENCE TO RELATED APPLICATIONS

The present invention claims priority from U.S. Provisional Patent Application No. 60/712,134, filed Aug. 30, 2005, and U.S. Provisional Patent Application No. 60/809,823, filed Jun. 1, 2006, the contents of which are herein incorporated by reference in their entirety.

BACKGROUND OF THE INVENTION

1. Field of the Art

The present invention relates to a combined input/navigational device used with the electronic medical record (EMR) and the Picture Archival and Communication System (PACS), and a method for its use thereof.

2. Description of the Related Art

In the traditional practice of radiologists and clinicians, computer applications in medicine are largely driven by input devices including the trackball, computer mouse, and keyboard. The end user uses one of these input devices in their interaction with the graphical user interface (GUI) to select a specific item or function to activate. This can take a number of forms, depending upon the training and practice of the specific end user.

For a radiologist interpreting medical images using a Picture Archival and Communication System (PACS), the input devices could direct a number of individual tasks including selection of a specific patient, imaging study, medical image, or mark-up and annotation of one or more images. Higher level tasks for the practicing radiologist would include selection of a specific tool or application to manipulate the image, navigate between individual images or entire studies, or activate decision support programs to assist with image interpretation.

The clinician, on the other hand, tends to be less image-centric, and more data-driven in their clinical orientation. The data points that need to be reviewed and processed in every-day practice come from a number of disparate sources including historical, physical, laboratory, pathology, and imaging examinations.

One of the key features that has minimized the widespread adoption of the electronic medical record (EMR) to date has been the reluctance of clinicians to embrace electronic reporting and communication. This is due to the simple fact that the user interface is not inherently intuitive to most end users and requires keyboard input, which typically is time consuming, labor intensive, and distracting to the majority of clinicians.

Most clinicians desire the ability to electronically edit or "mark up" various data, which can take the form of text, numerical, or graphical data. A cardiologist or neurologist requires the ability to highlight abnormalities on an EKG/EEG, an internist needs to highlight certain data points on the patient's chemistry profile, while the surgeon needs to graphically display surgical treatment planning.

In all these case, traditional input devices and text reporting becomes a limiting factor in allowing the physician to communicate pertinent thoughts and findings, which can often be better displayed through graphical representation.

In order to effectively navigate from one data source to another, clinicians need a reliable and time efficient input device that can be customized to their unique preferences and workflow patterns, regardless of the specific computer hardware being used.

Thus, an ideal interface and input device is desired that would allow for the clinician to maintain eye contact and concentration on the medical data itself, rather than input devices such as the computer mouse, keyboard, or track ball, or computer icons or pull down menus. Thus, the clinician would benefit substantially from the ability to translate free form thoughts and analysis and recommendations into the EMR.

Accordingly, developing a user-specific input device that is multi-functional, customizable and vendor neutral, to provide a means with which each individual end user can operate seamlessly and securely, with the potential to obviate the time and security demands associated with traditional input devices, would be of great benefit to the clinician.

SUMMARY OF THE INVENTION

It is one object of the present invention to provide an electronic stylus that serves as a combined input/navigational device used with the electronic medical record (EMR) and the Picture Archival and Communication System (PACS), and a method for its use thereof. The navigational device of the present invention provides the advantages of combining graphical and textual data input, and affords the end user expanded functionality, above and beyond data input alone.

The navigational device of the present invention includes the following main features: 1) portability (the navigational device can be transported by the end-user and directly integrated with any computer-based technology); 2) intrinsic memory (the navigational device would contain a memory chip to store user-specific preferences and protocols); 3) security (the navigational device would have a number of intrinsic security devices embedded within it, allowing for establishing user identity, such as: a) bluetooth technology; b) radiofrequency identification (RFID); c) handwriting recognition; d) physical manner in which the navigational device is held and used; and e) biometrics (retinal scan, signature blood flow); 4) direct, hands-on interaction between end-user and computer display, (as opposed to the indirect interaction that exists with a computer mouse).

The navigational device allows the user to have faster data input and navigation through patient records, to maintain eye contact and concentration on the task at hand, and the ability to improvise the specific type of input, which goes beyond existing icons, tool bars, pull-down menus. In particular, the navigational device allows the user to draw symbols and gestures, which can be mapped to structured text and navigational commands.

Further, the navigational device includes features such as pressure sensitivity (differences in the degree of applied pressure to the navigational device can be used for a number of different applications such as navigational speed and data prioritization; an electronic signature and verification of receipt of documents capability; and direct use of a color palette (which can be customized to user preferences) for identifying unique features and applications (i.e., electronic consultation and/or query).

In one embodiment consistent with the present invention, a navigational device for use with a touch screen of a computerized device, includes a main body having a writing point at one end; and a control mechanism, including: a microprocessor means; a memory means; a power means; and a pressure sensing mechanism which determines a pressure of said writing point on the touch screen.

The control mechanism may include a wireless transmission means which transmits data from the navigational device to the computerized device.

Further, the navigation device may include a camera means for performing photographic and scanning functions, and a sensing means to detect biometric information of a user. The sensing means may include at least one of a blood flow sensor, a voice recognition mechanism and a handwriting recognition mechanism.

Still further, the navigational device may include a color-coding means for assigning at least one of priority and access functions based on a predetermined color palette.

In another embodiment consistent with the present invention, a computer-implemented method of identifying and annotating an image from an electronic record displayed on a touch screen, includes the steps of displaying the image; utilizing a navigational device to identify and annotate the image; linking data from the electronic record to the image; and storing the annotated image in a database.

The step of identifying the image may include manipulating at least the image and the data on the touch screen utilizing the navigational device. Further, identifying the image may include the step of: detecting a pressure of said navigational device on the touch screen, wherein the pressure correlates to at least one of a predetermined speed, and a priority of images displayed on the touch screen.

Annotating the image may include embedding at least one symbol correlating to predetermined information, on the image. In addition, annotating the image may include color-coding at least one of the image and said data using a color-coding mechanism of the navigational device. The color-coding may correlate to at least one of priority, significance, and severity of information related to the image, or to at least one of privileges and access assigned to a user.

Further, a computer aided decision protocol may be used in annotating the image, and the image may be annotated with findings generated by said computer aided decision protocol. The findings may be color-coded to correlate to significance of said findings.

The annotations may be displayed as text in a report. The report may also be annotated with queries and requests for consultations, and graphical data with text and image-based data may be linked to the report. The report may be forwarded to predetermined recipients via a predetermined method.

In addition, security features of the present invention include performing a security protocol prior to displaying the image, to determine at least one of access and privileges related to a user of the navigational device. The security protocol may include biometric authentication of said user, such as at least one of a blood flow signature, a voice recognition protocol, a handwriting recognition protocol, and a retinal scan.

In another embodiment consistent with the present invention, a computer system having a program for identifying and annotating an image from an electronic record displayed on a touch screen, includes means for displaying the image; means for identifying and annotating the image; means for linking data from said electronic record to the image; and means for storing said annotated image in a database.

In addition, the computer system may include means for color-coding at least one of the image and the data, and means for performing a security protocol prior to displaying the image, to determine at least one of access and privileges related to a user.

Still further, the computer system may include means for detecting a pressure of the navigational device on the touch screen, wherein the pressure correlates to at least one of a predetermined speed, and a priority of images displayed on the touch screen.

In another embodiment consistent with the present invention, a computer system for identifying and annotating an image from an electronic record displayed on a touch screen, includes at least one memory containing at least one program including the steps of: displaying the image; utilizing a navigational device to identify and annotate the image; linking data from the electronic record to the image; and storing the annotated image in a database.

The program would also include the step of color-coding at least one of the image and the data using a color-coding mechanism of the navigational device, and performing a security protocol prior to displaying the image, to determine at least one of access and privileges related to a user. Further, the program would detect a pressure of the navigational device on the touch screen, wherein the pressure correlates to at least one of a predetermined speed, and a priority of images displayed on the touch screen.

In yet another embodiment consistent with the present invention, a computer-readable medium exists whose contents cause a computer system to identify and annotate an image from an electronic record displayed on a touch screen, the computer system containing a program which performs the steps of: displaying the image; utilizing a navigational device to identify and annotate the image; linking data from said electronic record to the image; and storing said annotated image in a database.

The computer-readable medium would include program steps to color-code at least one of the image and said data using a color-coding mechanism of the navigational device, and to perform a security protocol prior to displaying the image, to determine at least one of access and privileges related to a user. Further, the computer-readable medium would include program steps to detect a pressure of the navigational device on the touch screen, wherein the pressure correlates to at least one of a predetermined speed, and a priority of images displayed on the touch screen.

In yet another embodiment consistent with the present invention, a computer-readable memory device encoded with a data structure for identifying and annotating images using a computer system exists, the data structure having entries, each entry including a color from a color palette correlating to predetermined information on at least one of priority, significance, and severity of information related to the image, and access and privileges of a user.

In yet another embodiment consistent with the present invention, a computer-implemented method of identifying and annotating an image from an electronic medical record displayed on a touch screen, includes displaying the image on the touch screen; identifying medical issues shown in the image; annotating the image with at least one symbol correlated to predetermined information, using a navigational device; and prioritizing the medical issues using the navigational device. The prioritizing step may include color-coding at least one of the symbol and the image using the navigational device. Further, the navigational device may include a pressure detecting mechanism which determines at least one of a priority of the image and a speed of images displayed on the touch screen, based on an amount of pressure exerted by a user on the touch screen.

Accordingly, the electronic stylus or navigational device of the present invention has the advantages of both speed of information entry and review, accuracy, and may result in fewer repetitive stress disorders which are becoming increasingly prevalent with the use of the keyboards and mouse. These advantages will be particularly useful in healthcare information systems such as the electronic medical record and various other information and image management systems such as lab and radiology information systems, including navigation, communication, reporting, and security. By using the navigational device, end users can continue to focus on the image and clinical data available on the EMR without being distracted by less efficient paradigms that require pull down menus and location of various icons. This "eyes on" approach has the potential to increase workflow and productivity, decrease medical error rate, and decrease end user fatigue.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention relates to an electronic stylus as a combined input/navigational device for the electronic medical record (EMR) and the Picture Archival and Communication System (PACS), and a method for its use thereof.

The navigational device 100 (see FIG. 1) of the present invention and its method of use, differs from existing image management and information technology (PACS and EMR) software programs that utilize traditional input devices (mouse, keyboard, and track ball) as principal input devices, due to the "stylus-centric" approach to input/navigation. In the exemplary embodiment of the present invention, the navigational device 100 is designed to interface with existing information systems, such as a Hospital Information System (HIS) 200 (see FIG. 2), the Radiology Information System (RIS) 201, and PACS 202, and to conform with the relevant standards, such as the Digital Imaging and Communications in Medicine (DICOM) standard, DICOM Structured Reporting (SR) standard, or the Radiological Society of North American's Integrating the Healthcare Enterprise (IHE) initiative.

In addition, the navigational device is integrally utilized with Gesture Based Reporting (GBR), which is described in detail in U.S. patent application Ser. No. 11/176,427, filed Jul. 8, 2005, the contents of which are herein incorporated by reference in their entirety.

Figure 1:
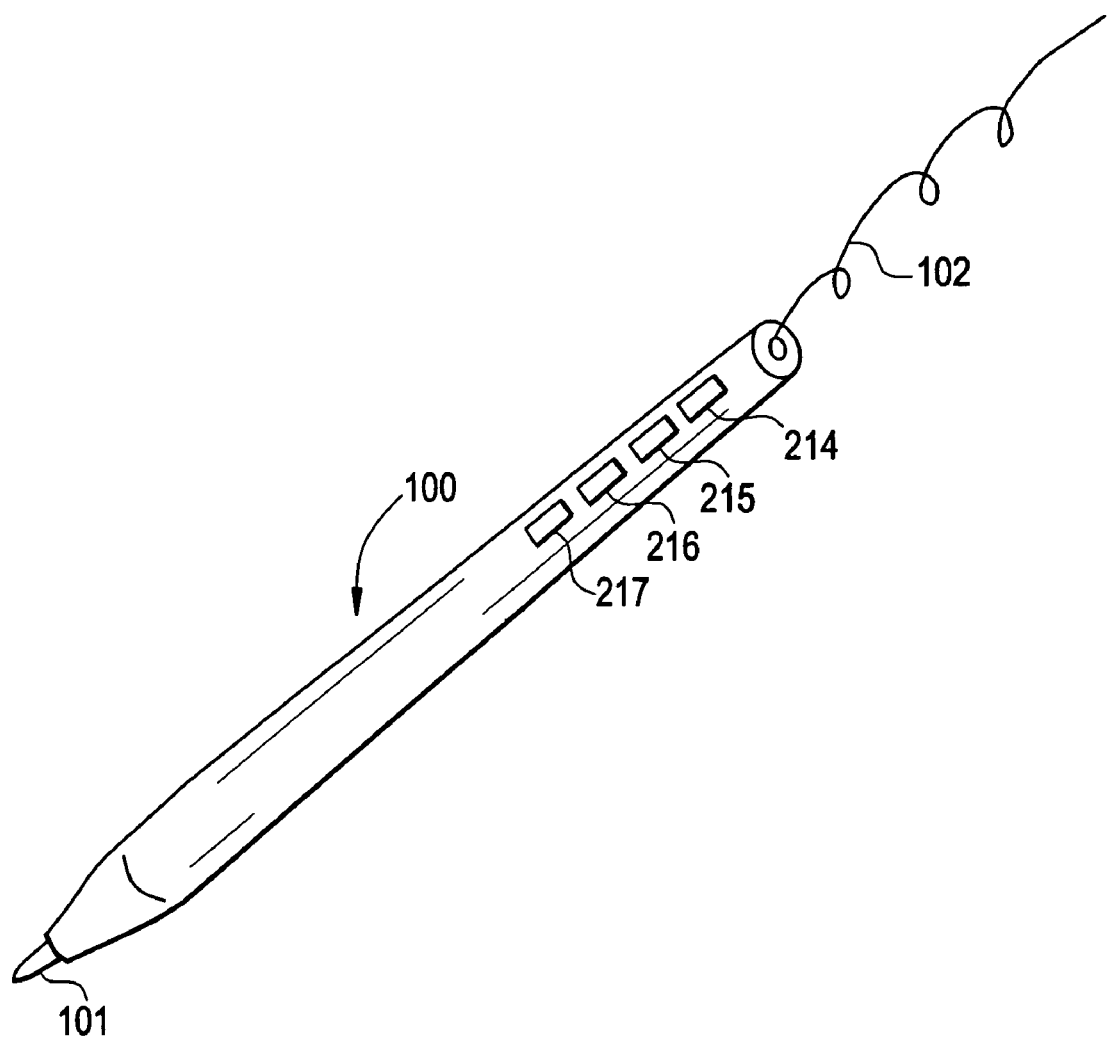
FIG. 1 shows a perspective view of a navigational device according to one embodiment consistent with the present invention.
Figure 2:
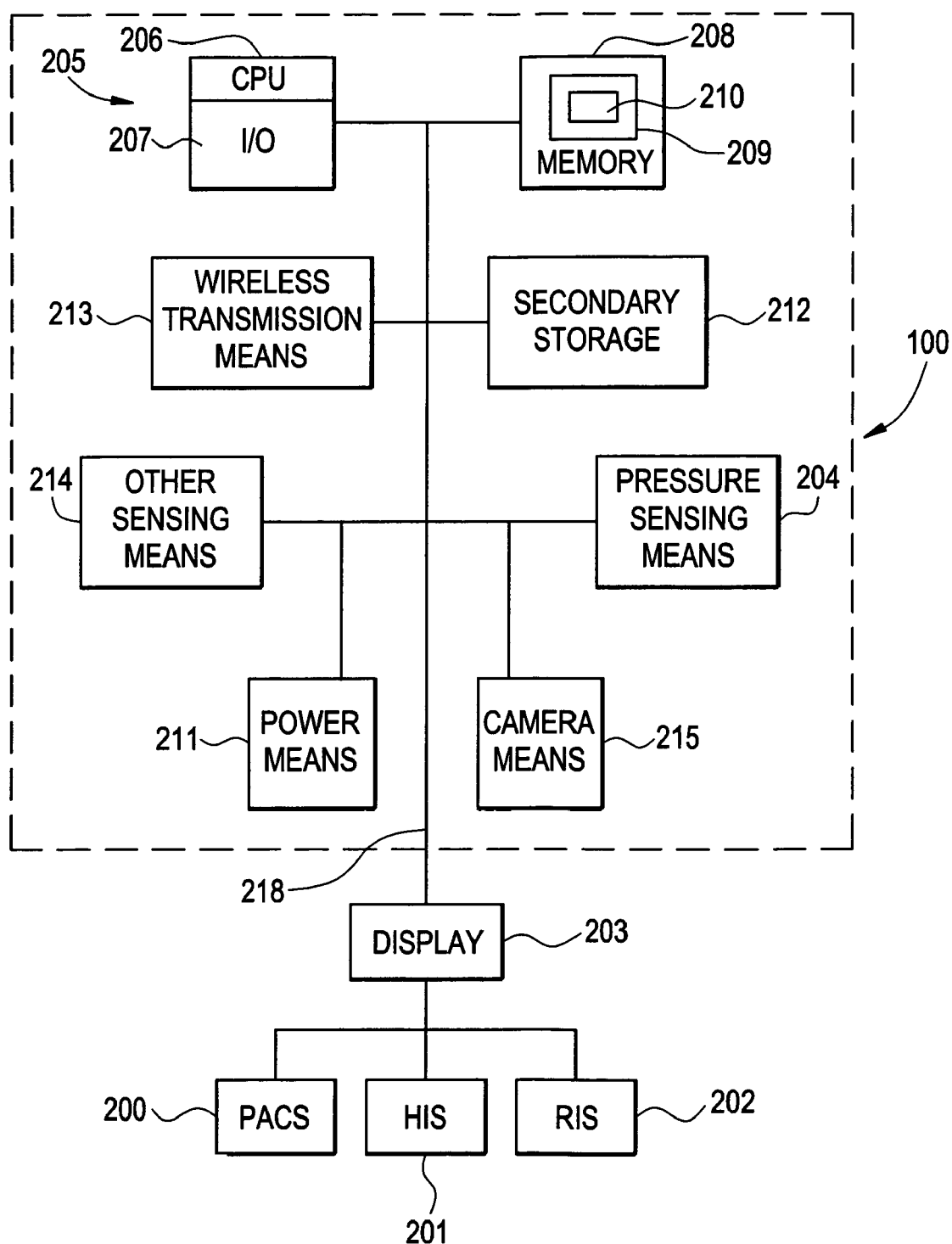
FIG. 2 shows a schematic of the elements which comprise the navigational device, according to one embodiment consistent with the present invention, and the system thereof.

As shown in FIG. 1, the navigational device 100 of the present invention, is shaped substantially like a pen, and is programmable (also by the user), portable and manipulated by a user. The writing point 101 may be shaped like a point, or like any type of instrument capable of being used on a touch screen of a display monitor 203 (see FIG. 2). The navigational device 100 can be used as a writing instrument or a control instrument to control functions on a display screen 203 of a computer or handheld computerized device.

Since the navigational device 100 can be used as a writing instrument, it may include within the instrument itself, a pressure sensing means 204 such as a pressure sensor, the pressure by the user on the writing point 101, which can be determined by a microprocessor means 205 (including a central processing unit (CPU) 206 or parallel processor and an input/output (I/O) interface 207), in order to institute a variety of features, such as navigational speed or data prioritization, for example. Alternatively, the touch screen or display monitor 200, can be sensitive to pressure, to achieve the same result. High-resolution touch screen computer monitors are currently available for commercial use.

The microprocessor 205 functions to execute a program 209 adapted to predetermined operations of the navigational device 100. The microprocessor 205 has access to a memory 208 for data storage, in which may be stored at least one sequence of code instructions comprising a program 209 and the data structure 210 therein, for performing predetermined operations. The memory means 208 or memory chip, stores the program 209 to perform the operations with respect to viewing and annotating images, for example, and to store user-specific preferences and protocols desired by the user. In addition, the navigational device 100 may include a secondary storage device 212, or the program 209 can be stored externally within a handheld computerized system, or the PACS device 200, in which case the navigational device 100 can be used solely as a writing instrument.

Note that at times the navigational device is described as performing a certain function; however, one of ordinary skill in the art would know that the program 209 is what is performing the function.

The program 209 which runs the operation of the navigational device may include a separate program code for performing a desired operation, or it may include a plurality of modules performing sub-operations of an operation, or there may be a single module of a larger program 209 performing the operation. Further, the may be a plurality of programs 209 corresponding to a plurality of operations being executed by the microprocessor 205.

The data structure 210 may include a plurality of entries, each entry including at least a first storage area that stores the databases or libraries of image files, or color palettes, as described below, for example.

The memory 208 or secondary storage 212, as storage means, may store at least one data file, such as image files, text files, data files, pressure ranges, etc., in providing a particular operation. The storage means 208, 212 may, for example, be a database, including a distributed database connected to a system, such as a handheld computerized system, or the PACS 200, via a network, for example. The database may be a computer searchable database and may be a relational database. The storage means 208, 212 may be also provided in an external system (i.e., a handheld system, or the PACS 200), and accessed via the navigational device 100 using a wire 102, or through a wireless communication system using wireless transmission means 213.

Thus, the navigational device 100 can be directly integrated with any computer-based technology, and can transmit data to a PDA, cellular phone, laptop, etc., via a variety of means, whether via wire 102 (which may be detachable) or wireless transmission means 213, including infrared (IR), radio frequency (RF), ultrasound, or digital cellular telephony. In addition, "bluetooth" technology can be used to transmit data from the navigational device 100 to a receiver (not shown).

In an alternative embodiment, a memory chip as secondary storage memory means 212, can be removed and uploaded into a computerized device, such as a PDA or laptop etc.

Further, although aspects of the present invention are described as being stored in memory, one of ordinary skill in the art would appreciate that all or part of the methods and systems consistent with the present invention may be stored on or read from other computer-readable media, such as secondary storage devices, like hard disks, floppy disks, CD-ROM, a carrier wave received from a network such as the internet, or other forms of ROM or RAM either currently known or later developed.

Power means 211 may be provided within the navigational device 100 by an internal battery. However, the navigational device 100 may be connected by a power cord 102 included in wire 102, to an external power source.

In addition, a camera means 215, including a photographic lens and flash mechanism, may be used to perform a retinal scan of a user, for user authentication using biometrics. The camera means 215 may also be used to scan the signature of the user for uploading into the system, or for bar codes or other uses. However, in an alternative embodiment, the camera means 215 is included in a handheld computerized device, or in the PACS 200.

Further, other biometric user authentication means may be included in the navigational device 100, such as a sensing means 214, such as a sensor to detect blood flow of the user, or an audio detector for voice recognition, and a handwriting recognition mechanism. Some means may be provided as hardware, and some means may be provided as software.

In addition, a color-coding means 216 (described below), and a control function button 217 (described below), may be provided on the navigational device 100.

Although the above-described features and processing operations may be realized by dedicated hardware, or may be realized as programs including code instructions executed on data processing units, it is further possible that parts of the above sequences of operations are carried out in hardware, whereas other of the above processing operations are carried out in software.

A bus 218 connects the various elements of the navigational device 100 together, and externally, to an imaging display screen 203. The connection is made via wire 102, or via wireless means 213 as described above.

Further, although specific components of the present invention have been described, one skilled in the art would appreciate that the system suitable for use with the methods and systems consistent with the present invention, may contain additional or different components, whether currently known or later developed, to achieve the same result.

Still further, although the apparatus and method of the present invention is described as being directed to use with digital images, some features of the present invention could be also adapted for use with analog images, such as conventional x-ray films, photographs, or paper-based images, with additional technology to recognize the handwriting, symbols, or gestures, based on the movement of the navigational device itself.

The imaging display screen 203 used with the navigational device 100 may be a high resolution touch screen computer monitor, which would allow images, such as x-rays, to be readable by the user, and for the symbols, gestures, or other annotations made by a user using the navigational device 100, to be applied easily and accurately. The touch screen 203 may be pressure sensitive and responsive to the input of the navigational device 100, in order to allow annotations to be made, for example, or to access certain features, such as a cine function described below.

The graphics user interface (GUI) of the present invention (which may be adapted to run on the computer operating system in use), may be ported to other personal computer (PC) software, personal digital assistants (PDAs), cell phones, and any other digital device that has a screen or visual component and storage capability. Further, the imaging display screen 203 may be provided on a tablet, pocket PC, and plasma screen, instead of a PACS 200 system.

The data being transmitted between the navigational device 100 and any computer-based technology can be encrypted by the program 209 for security purposes.

The navigational device 100 includes a plurality of security features embedded therein, which allows for establishment of a user's identity, such that no-one can not access a patient's records without the proper authority.

In one embodiment consistent with the present invention, the security feature of the navigational device 100 includes handwriting recognition software, such that the program 209 would analyze the handwriting of the user and compare it to a database of authorized users. If the handwriting is not that of an authorized user, the program 209 would terminate access to the EMR in a predetermined manner—including that of shutting down the computer or PACS 200, for example.

In another embodiment consistent with the present invention, the angle and pressure of holding and use of the navigational device 100 on the screen 203 as inputted by the pressure sensing means 204, and/or camera means 215, and/or other sensing means 214, would be analyzed by the program 209, and if the data did not fall within a predetermined range of use stored in the database 208/212, then the program 209 would terminate access to the user, or to the computer etc.

In yet another embodiment consistent with the present invention, biometrics can be used to determine the authenticity of the user—such as providing a blood flow sensor as another sensing means 214 (see FIG. 1) embedded within the navigational device 100. In this embodiment, the user's fingers would press a button 214 located on the navigational device 100, and the button 214, which accesses a sensor, would measure the blood flow of the user, and the program 209 would analyze the measurement to determine if it falls within a predetermined range (signature) of an authorized user. If not, the program 209 would terminate access to the EMR, etc., in a predetermined manner, including that of shutting down the computer or the PACS 200, for example.

In another example of biometrics, voice recognition software may be utilized by the navigational device 100 to analyze the voice of the user and compare the voiceprint to a database of authorized users. If the voiceprint is not that of an authorized user, the program 209 would terminate access to the EMR in a predetermined manner—including that of shutting down the computer or the PACS 200, for example.

In yet another example of biometrics, a retinal scan may be required before access is provided to the patient's EMR and use of the navigational device 100. The retinal scan may be performed by a camera means 215 on the navigational device 100 (see FIG. 1), or located externally—at the display screen 203, for example. The program 209 would compare the retinal scan taken by the navigational device 100, for example, with a database of retinal scans taken by authorized users, and if the comparison showed that the user is not included in the list of authorized users, the program 209 would terminate access to the EMR in a predetermined manner as above.

In yet another example of security features, bluetooth technology can be used, where the navigational device 100 transmits certain identifying data to a receiver in a handheld computerized device, for example, and the recognition of this data allows access to the EMR to the user.

In yet another embodiment, radiofrequency identification (RFID) can be performed where the navigational device 100 includes certain identifying data, which identifies the device 100 as the belonging to a predetermined user.

Specific features of the navigational device 100 will now be discussed with reference to the above elements which comprise the present invention, as described above. The features described allow the user to perform a myriad of functions in intelligent navigation and data handling, using the navigational device 100.

First, the pressure sensing means 204 of the navigational device 100 performs multiple functions that allow the user to control the viewing of images and to attach clinical significance to those images.

In one embodiment consistent with the present invention, based on the pressure applied by the user of the navigational device 100 (i.e., writing point 101) on the touch screen 203, the program 209 can calculate the pressure applied, and determine from the amount of pressure, different levels of priority (or clinical significance) of the findings being made by the clinician or radiologist. For example, when the user identifies an area of clinical significance on an image by circling what appears to be an abnormality with the navigational device 100 on the touch screen 203, the pressure sensing means 204 will determine the pressure being applied, and the program 209 would compare the results to the data in a pressure table provided in the database 208. If the program 209 determines that the pressure falls within a certain range, that range will correlate to a predetermined clinical significance (i.e., abnormal vs. normal), and a clinical priority (i.e., high, medium, or low priority). Thus, increased pressure of the navigational device 100 on the touch screen 203 will indicate a higher priority or higher clinical significance.

In another embodiment consistent with the present invention, the pressure sensing means 204 of the navigational device 100 may also be used to activate a cine function, where images presented on the touch screen 203 can be electronically scrolled (in a vertical fashion, for example), through different layers of data. In this embodiment, when the user has activated the cine function via a selection means (i.e., a pull-down menu, selection box, etc.), the pressure sensing means 204 will determine the pressure being applied, and the program 209 would compare the results to the data in a pressure table provided in the database 208. If the program 209 determines that the pressure is above a certain number, then the scrolling of the images will begin at a predetermined speed. As the pressure increases, the scrolling will increase in speed, up to a maximum speed that is still easy for the user to view.

The scrolling can be performed through multiple images or sequences of images in a medical imaging dataset, or multiple data sources within the EMR, as desired.

In another embodiment consistent with the present invention, the navigational device 100 can be used to identify unique features and applications (i.e., electronic consultation and/or query) by means of a color palette which can be customized to user preferences. For example, the navigational device 100 may include a color-coding means accessed by a button 216 (see FIG. 1), menu selection, or other means, with which each user may create their own customized colors and palettes to identify different user functions, severity of diagnosis, priority of case, or supporting technologies, etc.

Specifically, in one embodiment, different colors utilized by the navigational device 100, may denote different levels of clinical priority. For example, the color "red" may be classified as "emergent information, requiring immediate action by the designated physician", while the color "yellow" may denote information of "intermediate clinical significance" that requires review (and confirmation of receipt) within eight hours of posting. Further, the color "green" may denote "low clinical significance" that requires review within 24 hours of posting.

With a click of the button, the program 209 will show the user on the screen which color is being accessed (i.e., red, green, etc.). In an alternative embodiment, the button 216 will turn colors as it is depressed, so that the user is aware of which color is being accessed.

Once the user has designated an image or certain data by use of the color-coding means 216, the program 209 will automatically designate the images or data according to the color classification when storing the images or data. Further, the program 209 may automatically notify a predetermined recipient of the patient's EMR, by e-mail or message box or the like, of certain designations of clinical priority or severity of diagnosis.

In another embodiment consistent with the present invention, the navigational device 100 can be used for automated communication between a variety of sources including (but not limited to) physicians, administrators, technologists, clerical staff, or patients. For example, the user may draw a communication symbol on the touch screen 203 with the navigational device 100, to indicate a certain type of communication (i.e., e-mail), and/or may utilize a specific color to direct the communication in a predetermined manner. Thus, the color utilized by the navigational device 100 may indicate a "general" or "specific" communication.

In using the navigational device 100, the user may utilize the color-coding means 216 when selecting a form of communication to recipients. For example, a purple-coded, or "general" communication, would be one that the program 209 directs to all predetermined relevant clinicians involved in the patient's care, and an orange-coded, or "specific" communication, for example would be one that the program 209 directs to a predetermined specific user, such as a technologist, or a single physician only—all sent automatically by the program 209 based on the symbol designated for a predetermined communication preference (i.e., e-mail).

In another embodiment consistent with the present invention, the navigational device 100 may be used to assign a hierarchy of privileges based on the color palette chosen by the user. For example, when the user is selecting privileges to be assigned to a particular person, the user may utilize the color-coding means 216 to correlate predetermined privileges to the user.

For example, the color "green" chosen by the user using the color-coding means 216, may denote to the program 209 based on pre-authorized privileges stored in the database 208/212, that the specific data can be viewed by "all parties", while the color "red" may denote to the program 209 that the data can be viewed only by "physicians". Thus, if a user attempts to edit or perform functions outside of the predetermined privileges associated in the database 208/212 with the color-coding, the user would be denied access to the EMR etc.

In addition, these pre-defined EMR privileges can be directly integrated into the navigational device 100 and tied to the user's identification as discussed above with respect to the security features. Accordingly, once the authentication of the user has been performed using the biometric or other security features of the present invention, the program 209 will automatically assign a predetermined access to the user based on the privileges associated with that user in the database 208/212.

In one example of the feature of using a color palette and automated communication with the navigational device 100, a radiologist may review an imaging study on the touch screen 203, that has a quality assurance (QA) deficiency. The radiologist may draw a QA symbol using the navigational device 100, on the touch screen 203, with respect to a specific image, and assign a color scheme using the color-coding means button 216 for the transfer of the data, and the program 209 will automatically determine the priority of the communication, and to which authorized parties the data should be transferred.

In another example, the color-coding means 216 could be utilized to identify all the predetermined personnel in the QA queue. This could include the technologist performing the study, the imaging and hospital QA specialists, the radiology administrator, chief radiologist, and referring clinician. With a certain color code, all the predetermined personnel would receive a particular communication.

In addition, all resultant communications may be automatically electronically recorded and archived by the program 209 in association with the imaging study and patient's EMR once sent or received. In addition, any recommendations by the clinician (i.e., repeat exam), which is annotated into the EMR by the clinician using the navigational device 100, for example, can be tracked by the program 209 to ensure compliance. In this feature, the clinician checks a box or uses text recognition software for a repeat examination, and the program 209 will automatically schedule an e-mail reminder, for example to be sent to the radiologist or technician. When the action is performed (i.e., another imaging study is performed and stored in the database), the program 209 will automatically remove any flags for subsequent reminders.

Another feature of the navigational device 100, is the use of an overlay for decision support (i.e., CAD) for the user. Decision support tools, such as CAD mark-ups or user mark-ups, can be implemented (i.e., turned "on" and "off") by the program 209 through specific icons and symbols drawn by the user on the imaging study by the navigational device 100. The CAD mark-ups on the imaging study would be recognized by the program 209, and overlaid onto the medical image using a color chosen by the user utilizing the color-coding means 216 of the navigational device 100.

For example, if a radiologist elects to have certain CAD markers activated, he/she can use the color-coding means 216 of the navigational device 100 to identify a color (i.e., green) to instruct the program 209 to keep these CAD marks intact when the exam is reviewed at another time, and use another color (i.e., red) for the program 209 to remove those CAD marks the user deems irrelevant.

Accordingly, when a clinician reviews the same imaging exam at a later time, he/she can review what the CAD program marked (i.e., in blue), as well as what the radiologist marked (i.e., pertinent findings in green, for example, and irrelevant findings in red, for example) with the navigational device 100. The mark-up notated by each clinician can also be color-coded using the color-coding means 216 of the navigational device 100, for the purposes of subsequent review, notification or communication, by either the clinicians or the radiologists.

Further, this data can be used to track sensitivity/specificity of the CAD program and individual radiologists' interpretations, based on follow-up imaging studies, clinical management, and pathology reports. The program 209 will store the information for later analysis and reports, and changes to the default settings.

In another embodiment consistent with the present invention, the navigational device 100 may function as a bi-directional communication and signature device that allows for each unique end-user to electronically sign or verify receipt of electronic data. For example, after the data on the screen 203 is reviewed by the user, the user can affix his signature to the image using the navigational device 100, and the program 209 will verify the signature against a database 208/212 of signatures of authorized users, time stamp the signature, and permanently store the signature and its verification in the EMR, as well as in the end-users' queue.

In another embodiment consistent with the present invention, the navigational device 100 may be used to automate the generation of reporting templates by the physician.

For example, a radiologist would create a report for a brain MRI in a patient with the clinical indication of "seizures". The input for report generation can be symbols, gestures (using the navigational device 100), or speech, all of which can be recognized by the program 209 to correlate to a medical finding. The program 209 translates the symbols and gestures marked on the screen 203, and uses speech recognition software to translate the speech, into the form of a structured or prose text report, as desired.

The radiologist may utilize the navigational device 100 to archive this report in his/her report template queue and to list this report as "template for brain MRI seizures" for future search and access. The radiologist may also elect to have certain features of the report left blank, and may do so by underlining certain areas in the report using the navigational device 100, which can be "filled in" later on subsequent reports. Once this report template is finalized and the user indicates saving the report in the database 208/212, the program 209 will save the report in the database 208/212 and place the report into the report template queue. The report can be accessed by the program 209 as the default report by the radiologist directly, or the program 209 may present the report to the radiologist on future brain MRI requests with the clinical indication of "seizures".

In another example, a gastroenterologist would create a report in the EMR for a colonoscopy, which incorporates specific information regarding informed consent, conscious sedation, and the specifics of how the procedure was performed. In addition, the gastroenterologist may use a diagram to illustrate any specific pathologic findings and their specific location and appearance. The gastroenterologist chooses to use this report (using the selection means) as a "negative colonoscopy" template. Using the navigational device 100, the gastroenterologist can identify specific features or terms within the report to be left blank (by underlining using the navigational device 100), so that the blanks may be filled in on subsequent reports when the program 209 accesses the report again upon user request.

In another embodiment consistent with the present invention, the navigational device provided an editing function to highlight and save critical data.

Specifically, the navigational device 100 allows for each end-user to create their own set of symbols and gestures for editing and saving data in the EMR. This predetermined set of symbols and gestures are recognized by the program 209 and can be saved in the database 208/212, and when utilized by the user, the notated data for being "saved" can then be copied and transferred by the program 209 to patient specific progress notes, data sheets, or consultations, as identified by the user. Once the desired data is highlighted by the end-user, a symbol or gesture can direct where the copied data is recorded by the program 209.

In one example, the program 209 may save and copy "key" clinical, imaging, and laboratory data into a patient radiology folder, as directed by the radiologist using the navigational device 100, for the data to be reviewed on subsequent imaging studies. For an oncology patient receiving treatment for metastatic breast carcinoma, this folder would be periodically updated by the program 209 as directed by the radiologist, based on new imaging findings and clinical treatment available in the EMR. In addition, the radiologist can instruct the program 209 to automatically update the patient's radiology folder in the EMR by incorporating key data points whenever new information is posted by the program 209 on the EMR.

In another example, a family practitioner may edit specific data from disparate informational sources (i.e., pathology reports, pharmacology, imaging reports, laboratory data, oncology consultation) using the navigational device 100, to copy into a patient oncology summary. The summary is automatically accessed by the program 209 whenever the patient reports for an oncology-related visit and their EMR is accessed using the navigational device 209. The oncologist in turn, could incorporate relevant clinical, imaging, and research data essential to the patient's treatment regimen, using the navigational device 100. When newly published clinical trial data is identified (i.e., through automated searches of MedLine and the National Library of Medicine (NLM) by the program, for example), the oncologist can take edited excerpts and electronically link this to the patient's oncology summary using the navigational device 100.

In other embodiments consistent with the present invention, electronic consultation and queries are additional features provided by the navigational device 100.

As discussed above, communication needs to be hierarchical, instantaneous, and verifiable within the EMR and the electronic navigational device 100 serves as the means to facilitate these tasks. As noted above, the hierarchy can be established through different means (i.e., color coding, pressure sensitivity, symbols), and allows the healthcare provider to link priority status with the information or query being conveyed.

In the present invention, each user has a pre-defined communication protocol which has been created according to their unique preferences. Further, the navigational device 100 may be used to direct electronic communication of findings and consultations to predetermined recipients.

An electronic directory/database of referring/consulting physicians can be created within the program 209 of the navigational device 100, with a defined communication pathway (i.e., text page, e-mail alert, autofax, etc.). The program 209 would record the data communicated to the intended recipient in the database 208/212 along with the date and time of the communication. The receiving party would electronically acknowledge receipt of the electronic transmission and send an electronic confirmation receipt, which is recorded by the program 209.

Further, users may direct to have all consultations or queries sent via text paging by the program 209, while other users may request that the program 209 send all high priority and "stat" consultations to their cell phone directly, with non-priority consultations sent to them by the program 209 via e-mail.

With the above, the navigational device 100 becomes a portable computer, with the electronic communication record transferred directly to the patient's EMR. This communication protocol can be directly linked or placed in memory 208/212 of the navigational device 100, so that regardless of the computer or location being used, the consultation feedback loop remains intact.

In another embodiment, the navigational device 100 can be used by an authorized person with clinical privileges to order additional testing. The user can graphically and quickly respond to a recommendation in a progress note, radiology report, or consultation and place an order using a specific symbol or gesture on the screen using the navigational device 100. The program 209 would recognize the symbol or gestures, and automatically place an order to the relevant party to have the test scheduled.

For example, a clinician reading a brain MRI report with recommendation for follow-up study in 3 months can electronically circle the recommendation and place a check mark using the navigational device, which electronically instructs the program 209 to place an order for brain MRI in 3 months. The order is placed by the program, 209 and verified by the program 209 with a date and time assigned to the study. The EMR program of the PACS 200 (or the program 209) then generates a confirmation receipt to the ordering clinician, notifying him/her that the exam has been scheduled, and automatically forwards a notification e-mail to the patient.

In another example, a clinician reading a cardiology consultation reviews the summary and notes the following recommendations for clinical management/testing:

1) Stress echocardiography to assess cardiac wall motion and ejection fraction; 2) change in medical regimen by discontinuing one medication and adding a new one in its place; 3) change in diet to low sodium; 4) screening CT for coronary arterial calcification scoring; and 5) follow-up appointment with the consulting cardiologist in 3-4 weeks.

The clinician responds to the recommendation list by electronically verifying certain orders and deleting others on the touch screen 203 using the navigational device 100, and instructing this order list to be reported back by the program 209, to the consulting cardiologist. This would be accomplished by the clinician, for example, drawing a box around the recommended list on screen 203 and drawing a line through items #2 and 4, followed by an "X", for example, which would instruct the program 209 that these recommendations are to be deleted. The clinician may circle items #1, 3, and 5, followed by a "check mark", which would instruct the program 209 to place these orders. At that time, the clinician may place a slash mark through the number "3" in item #5, and circle the number "4" followed by a "check mark". This instructs the program 209 that it should schedule a follow-up appointment in 4 weeks. These actions are then signed digitally and verified by the clinician using the navigational device 100, using the electronic signature and verification protocol above.

In another example, an internist may be reviewing chemistry results from a patient's blood test on the screen, and may notice a critically high white blood cell (WBC) count. The clinician circles the elevated WBC value using the navigational device 100, and through a specific set of symbols, the program 209 would recognize that a series of orders are being placed that include, for example, the symbols for: 1) Repeat WBC count "stat"; 2) microbiology cultures and sensitivity of urine, blood, and sputum; 3) chest X-ray; and 4) infectious Disease consultation.

In yet another embodiment of the present invention, the navigational device makes possible the identification of "key images" from medical imaging studies (which includes endoscopy, intra-operative photography, pathology, etc.), by identifying certain images by symbols correlating to "key image", and by using the navigational device 100 to navigate to the annotated "key images", and to highlight the specific images desired.

In another embodiment consistent with the present invention, the navigational device 100 may be used to accomplish "intelligent navigation".

Since the volume and complexity of EMR data continues to expand, and it is difficult for end users to navigate through large and expansive data repositories to find the information of specific interest, and although vendors have attempted to categorize data in a logical and chronological fashion, it is often cumbersome and time consuming to find the specific data of interest. In the long run, this often limits end user compliance, and leads to inefficient data access.

As an example of "intelligent navigation", the radiologist uses the navigational device 100 to select the "anatomic man" icon on the screen 203 and places the navigational device 100 over the thorax. The program 209 would recognize the anatomic region of interest and through a series of pop-up menus on the screen 203, would ask the end user to select the specific type of data (i.e., imaging), specific type of test (i.e., CT), pathology (i.e., lung cancer), and location (i.e., all) for access.

Once the radiologist makes his selection, the program 209 will access the database 208/212 and identify, for example, 12 prior CT exams that were performed in association with "lung cancer" and would present this list on screen 203 (with linked images and reports, for example) to the radiologist for review. The radiologist in turn, would use the navigational device 100 to open up the desired studies and format them on the monitor 203 based on his/her unique preferences. This entire sequence would take less than 30 seconds using the "intelligent navigation" of the present invention, and would require >3 minutes, for example, through conventional means. In all likelihood, the end user would have aborted the search prematurely due to time constraints and frustration, in that time.

In another example of "intelligent navigation" using the navigational device 100 of the present invention, a thoracic surgeon would search the database 208/212 for information regarding prior surgical and radiation treatment for lung cancer on a specific patient. The surgeon also would begin the search by accessing the "anatomic man" icon on the screen 203, and would place the navigational device 100 over the thorax. Using the same program-generated pop-up menus, the surgeon selects pathology (i.e., lung cancer), specific data (i.e., operative notes, consultant reports—radiation therapy), treatment regimen (i.e., surgery, radiation therapy), and location (i.e., all). The program 209 would then provide the surgeon with all surgical and radiation therapy reports along with links to imaging studies and reports, on screen 203.

In yet another example, an oncologist treating the same patient for tumor recurrence goes through the same procedure, but is interested only in prior medical treatment of lung cancer. Using the navigational device 100 and prescribed workflow, the oncologist selects from the data on-screen 203, the pathology (i.e., lung cancer), specific data (i.e., consultants report—medical), treatment regimen (i.e., medical, experimental), and location (i.e., all, NLM) desired. In addition to the patient's information concerning past medical treatment for lung cancer, the program 209 would search the NLM database to identify articles in the peer review literature for experimental treatment of lung cancer with links to the abstracts and present them to the user on screen 203.

In this example, "intelligent navigation" allowed the end user to access targeted clinical data from the EMR along with external data relevant to the clinical question at hand. This improves the quality of healthcare by linking disparate information sources in a timely and efficient fashion. In this same example, a similar search of the Medical Image Resource Center (MIRC) by the program, would have allowed the radiologist to access other medical imaging studies of lung cancer from its online archive.

As noted above, many features are preprogrammed into the navigational device 100. In particular, in one embodiment as mentioned above, the navigational device 100 can contain user-specific preferences, which can be used for multiple functions including display protocols, navigation, interpretation, and communication. The program 209 will automatically continuously update the user-specific preferences and modify them based on the integration of an electronic auditing tool functionality in the navigational device 100. This in effect, allows all navigational device-initiated electronic commands to be recorded by the program 209 for analysis.

This means that the users preferences, such as type of report, type of communications, that are used in reports, would be automatically presented as the default option to the user by the program 209 based on past historical use.

Further, the tool bars and icons that currently constitute the computer graphical user interface (GUI) could be electively removed and replaced by user-specific customized preferences. These preferences could be activated in one of two ways, for example:

1) Activating a button 217 (see FIG. 1) on the navigational device 100 (analogous to a "right click" on a computer mouse), which displays the tool bar on screen 203; and 2) Auto-populating the tool bar onto the touch screen 203 (in a pre-determined location), and allowing the user to manually activate the desired tool functions using the navigational device 100.

These customized tools and applications could be modified by the program 209 in accordance with predetermined protocols, for the specific task at hand.

For example, a radiologist may have different tools and applications in accordance with the specific type of imaging exam (e.g., CT), anatomic region (e.g., chest), and the clinical indication (i.e., rule-out lung cancer). In this specific example, the radiologist may elect to have the program 209 incorporate automated decision support functions (i.e., CAD and automated measurements, as mentioned above) into the default template.

In another embodiment, the electronic navigational device 100 could also provide the functionality to allow alternative protocols to be automatically "downloaded" into the navigational device's 100 memory 208/212 and activated by specific commands.

For example, one radiologist may find a colleague who has developed a specific navigational/display protocol for evaluating pulmonary embolism on chest CT angiography. The radiologist may desire to incorporate this "new" protocol into his/her automated preferences by simply downloading the data inputs that define this new protocol and instructing the navigational device 100 to utilize this new protocol with the written command of "PE", for example, or via a selection means. The next time that the radiologist is reviewing a chest CT angiography exam for pulmonary embolism, he/she simply writes the letters "PE" on the screen with the navigational device 100, and the program 209 will be instructed to use the newly defined protocol for the various functions of image display, navigation, tool functions, decision support, and communication.

In another embodiment consistent with the present invention, the navigational device 100 includes an electronic auditing tool program, and the program 209 can systemically analyze the data to determine new short-cuts or alternative protocols, based on each individual user's workflow. This workflow data can be pooled by the program 209, with other users' data (based on a number of variables including exam type, clinical indication, pathology, etc.), in an attempt to identify "short cuts" and "best practice" guidelines. Once determined, the program 209 can present these community-wide "streamlined" protocols to the individual user as alternative default protocols. If the user elects to use these "streamlined" protocols, they could be incorporated into the program 209 as the new default templates.

In operational use (see FIGS. 3A and 3B) of the navigational device 100, the radiologist may wish to review an RIS worklist of unread studies and use the navigational device 100 to select a specific unread exam, which may, in one example, consist of a brain MRI in a patient with multiple sclerosis, or an EKG in another example.

Figure 3A:
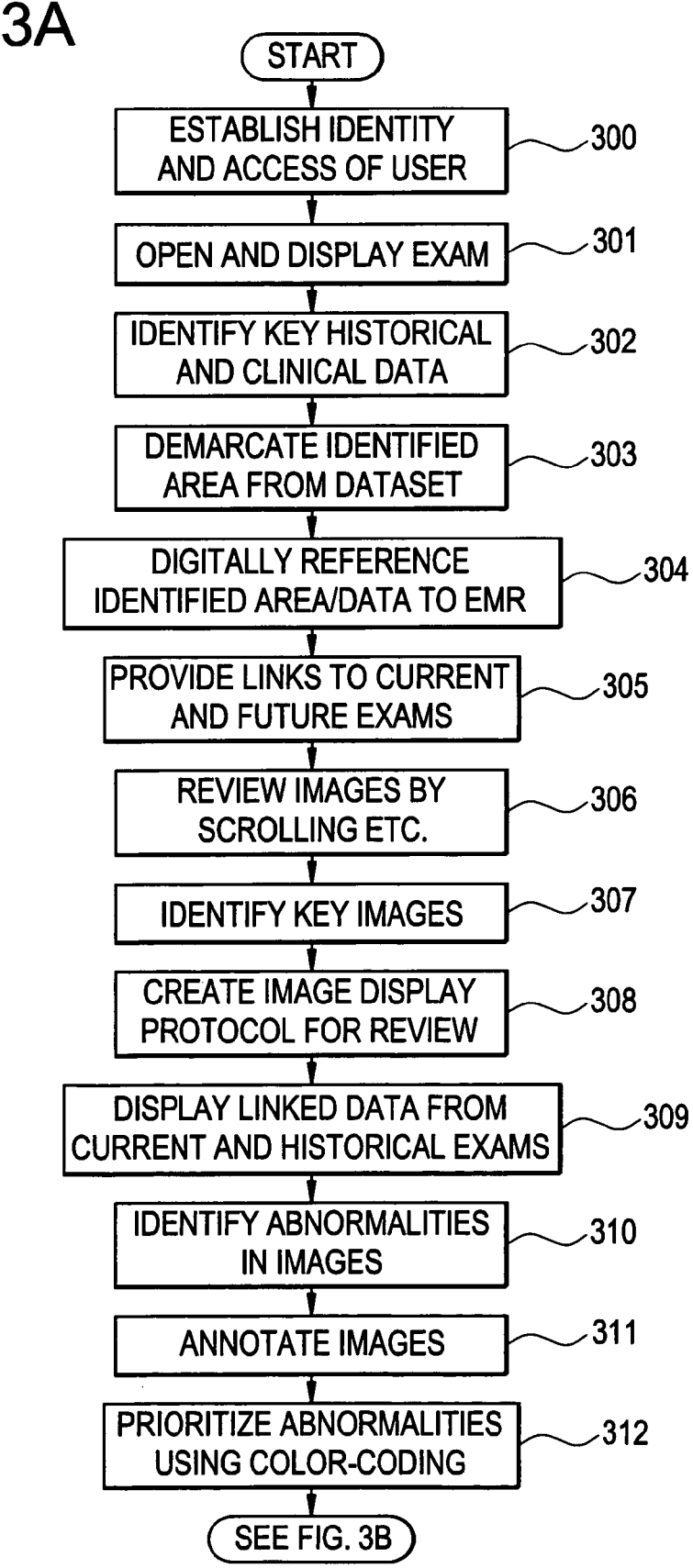
FIGS. 3A and 3B show a flow chart of the steps involved in operating the navigational device, according to one embodiment consistent with the present invention.

In step 300, the program 209 will establish the identify, privileges, and access of the user, utilizing at least one of the security features provided (see FIG. 3A).

In step 301, after the program 209 establishes the identity, access, and privileges etc., of the user, the program 209 will open the specified exam and display it on the monitor 203.

Then, the radiologist, in step 302, can use the navigational device 100 to identify key historical and clinical data from the patient's EMR by underlining or circling noteworthy data for subsequent indexing to the patient EMR. If the area for attention is an abnormality, for example, the user can utilize the navigational device 100 to highlight the area of abnormality by circling that area on the EKG data.

In step 303, the program 209 would recognize the highlighted area, and would automatically demarcate the highlighted area from the overall dataset.

Once the relevant area is highlighted, the user can then access a command on the display screen 203, using the navigational device 100, and this segmented data can then be digitally referenced (using an XML schema, for example) to the patient's electronic medical record in step 304.

Thus, in step 304, the program 209 will locate the patient's electronic medical record based on identifying information on the image being viewed, and display it on the screen 203.

In addition, the program 209, in step 305, can provide links to current and future imaging exams, which are automatically updated on a periodic basis by the program 209, including displaying an updated review of systems and key clinical findings. Accordingly, the patient's electronic medical record can be quickly and easily accessed by all clinicians, who may not have the time or expertise to review the patient's medical records in their entirety.

Once the current and historical exam displays have been activated using the navigational device 100 in step 305, the radiologist may determine the speed and manner in which to navigate through the imaging dataset.

For example, using the pressure sensitivity function of the navigational device 100, the radiologist can activate the cine function within a specific imaging sequence (e.g., T1 axial images). This is accomplished by the user simply pressing down with the navigational device 100, on the touch screen 203, and in step 306, the program 209 will then start to scroll the images sequentially on the screen 203. The rate of speed can be controlled by releasing the pressure on the screen 203 by the navigational device 100, to slow down the images. In an alternative embodiment, the control button 217 provided on the navigational device 100, may be utilized to provide the cine function.

Release of pressure of the navigational device 100 from the touch screen 203, will make the program 209, in step 307, slow and then stop the image display, such that the radiologist may review the images and identifies "key images" with pathology.

The radiologist can then use the navigational device 100 to select the specific imaging sequences to review and can use the "click and drag" functionality of the navigational device 100 to create the image display protocol for image review, in step 308. For example, the navigational device 100 can be placed over the image desired, and the control button 217 on the navigational device pressed, and the program 209 will acquire the image and translate it across the screen 203 to the desired location where the button 217 on the navigational device 100 is released to release the image.

In step 309, the program 209 can link data from current and historical exams, in response to the radiologist's selection, by directing the program 209 to display the desired historical exam image(s) on one portion of the screen 203, while the current exam image is displayed on a different portion of the screen (or in another embodiment, the two images are displayed on different screens).

Note that the radiologist has the capability of electing to make this specific display protocol the standard default for future exams, by invoking the icon or symbol for default display protocol which is displayed on the screen 203 by the program 209.

By utilizing these steps, the program 209 of the navigational device 100 uses the information for peer review or quality control purposes, by identifying agreement with previous studies, quality of images, or other acquisition issues.

In another example of presentation of the images desired on the screen(s), the radiologist may utilize the navigational device 100 to select a 4 on 1 image display format for the display screen 203, and the program 209, may display a stacked T1 weighted axial sequence in the upper left hand corner of the screen 203, for example, and a T2 weighted axial sequence in the upper right hand corner of the screen 203, for example. A sagittal FLAIR sequence may be displayed by the program 209 in the lower left hand corner of the screen 203, for example, and the sagittal T1 post-contrast sequence may be displayed, for example, in the lower right hand corner of the screen 203. Each image is manipulated using the navigational device's "click and drag" function 217.

In yet another embodiment, the navigational device 100 can be used to electronically "link" two sets of images for review in tandem, where the anatomy from each sequence is reviewed at comparable levels. The navigational device 100 can secure the desired images using the "click and drag" function as described above, and with the selection of a "link" icon, the program 209 will present the images in tandem, allowing the radiologist to review two separate sequences (T1 and T2 axial, for example) in a single plane, similar sequences in different planes (T2 axial and T2 sagittal, for example), or current and historical comparable sequences in a single plane (T2 axial current and prior, for example).

In reviewing the images presented on the screen 203, the user can utilize the navigational device 100 to draw a predefined graphical symbol or gesture (i.e., a five-pointed star)

to describe the abnormality in question that is presented in the image, and the program 209, in step 310, will utilize character/handwriting recognition software, to translate the symbol into the medical language which describes the abnormality and will annotate the patient's electronic medical record with the corresponding description.

The advantage of a system that accepts graphical input (in the forms of symbols and gestures) to help analyze and highlight abnormalities, where the symbols or gestures are easily transcribed into an abbreviated preformatted report, lessens the time the clinician has to spend preparing reports. Using graphical representation through icons, symbols, and gestures, the program 209 may direct the EMR to automate the search of specific information based on a number of variables including (but not limited to), date/time, anatomic region, specific type of test or data, pathology or specific medical condition, treatment regiment, location, and key findings.

In step 311, the user can annotate any specific features within the image of interest, and the program 209 will highlight and copy and index any "key image" or portion thereof.

In step 312, the user can utilize a pre-defined color coded system (which can be either embedded within the navigational device 100 as button 216, or accessed by a symbol on the screen 203), and the program 209 will prioritize, for example, multiple abnormalities in question, using the appropriate color code (i.e., red for clearly abnormal, yellow for possibly abnormal, green for normal, for example). In another embodiment, numerical coding can be used instead of color-coding.

Figure 3B:
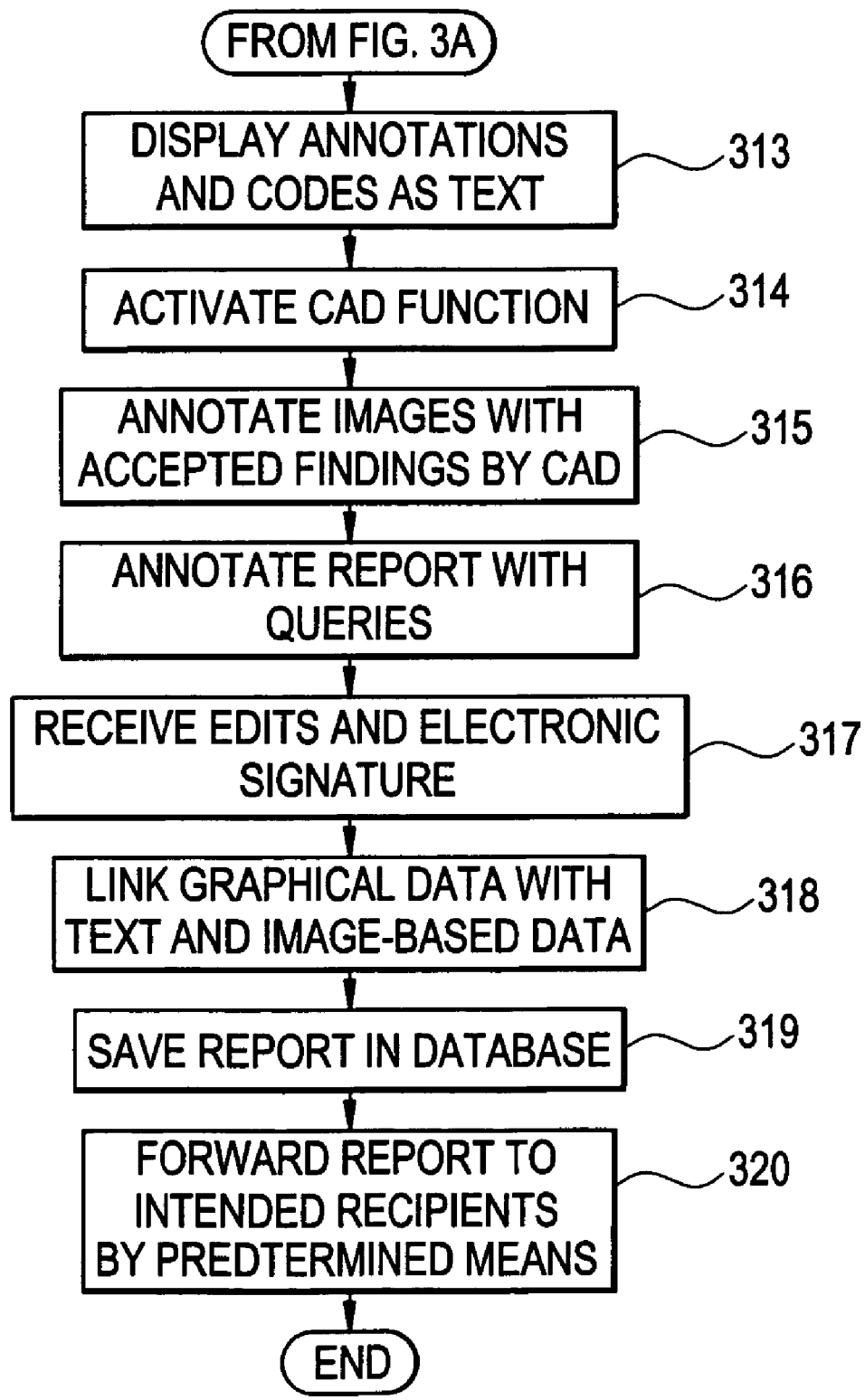

Subsequently any annotations can be reviewed by the user by accessing various filters or windows into the data that are shown on the screen 203, using the navigational device 100, such that the program, in step 313, displays the information as conventional text (see FIG. 3B).

Before completing the interpretation/reporting process, the radiologist may elect to engage the use of decision support software (i.e., computer-aided detection (CAD)) to assist with image interpretation. Using the navigational device 100, the radiologist may activate the CAD function in step 314, for example, and review the highlighted areas of abnormality. The color-coded (or numerical coded) capability of the navigational device 100, as noted above, can then be noted by the program 209 to selectively "accept" or "reject" the areas identified by the CAD software and incorporate the "accepted" findings into the annotated "key images" in step 315. For example, an area in red can be detected by the CAD software and "accepted" as findings in the annotated "key image" by the program 209. However, an area in green, for example, would be "rejected" by the program 209 and not included in the findings.

The radiologist and end user have the added capability of "turning on" and "turning off" these annotations (which can also be color coded to determine priority), using the navigational device 100.

In addition, the user can utilize the navigational device 100 to generate electronic queries and consultations by encircling the area of concern and then using an appropriate symbol (i.e., question mark) to denote a query. The questioner uses the navigational device 100 to formulate his or her query (using either pre-defined symbols, gestures, or handwriting). The queries are then annotated into the report by the program in step 316. This navigational device-induced bidirectional electronic consultation can be "turned on and off" by the program 209, based on end-users' preferences.

The radiologist can then use the navigational device 100 to edit the structured text report (using the usual word-processing editing features) and electronically sign the report in step 317.

In step 318, the program 209 can link graphical data (i.e., EKG data), with other text and image-based data within the EMR (i.e., medical regimen, cardiac imaging studies, highlighted data from the cardiology consultation report and H & P, etc., for example).

In step 319, the program 209 will save the edited and signed report, with linked images, in the database 208/212.

In step 320, the program 209 can make the report and accompanying "key images" available to the referring clinician upon the instructions of the user identifying the intended recipient(s). The program 209 will electronically generate the combined text-image dataset using a predefined results reporting format, which has been customized to the specific preferences of the referring clinician. The predefined results reporting format and communication protocol can take a number of forms including e-mail alerts, PDA, text paging, cell phone, or electronic fax, to the recipient, which are automatically generated by the program 209 based upon predetermined preferences.

The use of an electronic stylus or navigational device as a single, integrated input device to provide text and graphical input lends itself to a variety of applications within the medical domain. Graphical representation and reporting is by no means limited to radiologists. Medical images are used in a wide variety of disciplines including dermatology, pathology, gastroenterology, neurology, and virtually all forms of surgery. In addition, graphical displays for reporting and consultation can be used for diagramming pertinent clinical findings within the history and physical (H & P), consultation, operative, and procedure notes. This type of input and display represents a better representation for demonstrating pertinent anatomy, in comparison to traditional text-based reporting. The navigational device of the present invention allows the end-user to combine the functionality of text, graphical, and color coded input within the EMR.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer-implemented method of identifying and annotating a radiological image from an electronic medical record displayed on a touch screen, using a pen navigational device, comprising:
  displaying a medical image on the touch screen of a computer monitor of a client computer;
  receiving an instruction to link data from the electronic medical record (EMR) of a patient, which is stored in a database of one of a client computer or server computer, to the image on the touch screen;
  providing a color coded system in the pen navigational device, such that the pen navigational device can utilize color coding to identify, annotate, and prioritize portions of the image on the touch screen;
  wherein said color coding includes identifying different levels of clinical priority requiring action, on said image;
  calculating a pressure applied by the pen navigational device on the touch screen using a pressure sensing means at the client computer, in order to determine an amount of pressure applied, said amount of pressure which indicates one of said different levels of clinical priority requiring action, an increased pressure indicating a higher level of clinical priority with a corresponding predetermined color coding, and a decreased pressure indicating a lower level of clinical priority with a different corresponding predetermined color coding;

displaying the annotated image with each of said different levels of color coding representing each of said different levels of clinical priority; and receiving and storing said annotated image with said different levels of color coding, in said database.

2. The method according to claim 1, wherein identifying the image includes manipulating at least the image and said data on the touch screen utilizing said pen navigational device.

3. The method according to claim 1, wherein the image includes at least one embedded symbol correlating to predetermined information, on the image.

4. The method according to claim 1, wherein annotating the image includes demarcating portions of the image and said data for additional scrutiny.

5. The method according to claim 4, further comprising:
compiling, using processing capability of the client computer, and displaying on the computer monitor, said annotations as text in a report.

6. The method according to claim 5, further comprising:
receiving annotations on said report with queries and requests for consultations.

7. The method according to claim 5, further comprising:
automatically affixing an electronic signature to said report.

8. The method according to claim 5, further comprising:
linking graphical data with text and image-based data to said report at said client computer.

9. The method according to claim 5, further comprising:
automatically forwarding said report from said client computer, via a predetermined method related to said color-coding, to predetermined recipients.

10. The method according to claim 1,
wherein said amount of pressure correlates to a predetermined speed of images displayed on the touch screen, with increased pressure relating to a faster speed, and decreased pressure to a slower speed.

11. The method according to claim 10,
wherein said increased pressure allows scrolling through images displayed on the touch screen;
wherein increased pressure translates to relatively faster scrolling than decreased pressure, which translates to relatively slower scrolling; and
wherein a release of pressure makes the scrolling stop.

12. The method according to claim 1, further comprising:
receiving activation instructions at said client computer to activate a computer aided decision protocol to automatically annotate the image.

13. The method according to claim 12, further comprising:
automatically annotating the image with findings generated by said computer aided decision protocol.

14. The method according to claim 12, wherein said automatic annotation includes applying CAD markers to the medical image, and said CAD marks are color-coded such that predetermined color-coded CAD marks are kept intact for further review, and other predetermined color-coded CAD marks are removed.

15. The method according to claim 1, further comprising:
performing a security protocol at said client computer, prior to displaying the image on the touch screen, to determine at least one of access and privileges related to a user of said pen navigational device.

16. The method according to claim 15, wherein said security protocol includes biometric authentication of said user.

17. The method according to claim 16, wherein said biometric authentication includes at least one of a blood flow signature, a voice recognition protocol, a handwriting recognition protocol, and a retinal scan.

18. The method according to claim 17, further comprising:
scanning items including at least bar codes, retinas, and signatures, using a camera means.

19. The method according to claim 17, wherein said blood flow is measured using a sensing means.

20. The method according to claim 1, wherein said color-coding correlates to at least one of priority, significance or severity of clinical information related to a radiological image of a patient.

21. The method according to claim 1, wherein said color-coding correlates to at least one of privileges and access assigned to a user.

22. The method according to claim 13, wherein said findings are color-coded to correlate to significance of said findings.

23. The method according to claim 1, further comprising:
displaying data on said touch screen, from a database related to the image, upon information entered by a user at said client computer;
wherein said data includes links to other electronic records.

24. The method according to claim 1, further comprising:
automatically identifying user preferences as default operational protocols.

25. The method according to claim 1, further comprising:
utilizing intelligent navigation of said pen navigational device to recognize areas of interest on graphical representations on the touch screen;
accessing said areas of interest on said graphical representations on the touch screen; and
instituting searching of said database for information on said areas of interest.

26. The method according to claim 1, further comprising:
performing auditing of said data to provide streamlined or alternative protocols to the user.

27. The method according to claim 1, wherein said pen navigational device is programmed with user-specific preferences for navigation and communication.

28. A computer system having a program for identifying and annotating a radiological image from an electronic medical record displayed on a touch screen, using a pen navigational device, comprising:
a touch screen of a computer monitor of a client computer, which displays the medical image thereon;
a database of a client computer or a server computer which stores electronic medical records of a patient;
means for providing color coding system in the pen navigational device, such that the pen navigational device can utilize color coding to identify, annotate, and prioritize portions of the image on the touch screen;
wherein said color coding includes identifying different levels of clinical priority requiring action, on said image;
pressure sensing means for calculating a pressure applied by the pen navigational device on the touch screen at the client computer, in order to determine an amount of pressure applied, said amount of pressure which indicates one of said different levels of clinical priority requiring action, an increased pressure indicating a higher level of clinical priority with a corresponding predetermined color coding, and a decreased pressure indicating a lower level of clinical priority with a different corresponding predetermined color coding;

wherein said computer monitor displays the annotated image with each of said different levels of clinical priority; and wherein said database stores said annotated image with said different levels of color coding.

29. The computer system according to claim 28, further comprising:
means for performing a security protocol prior to displaying the image, to determine at least one of access and privileges related to a user.

30. The computer system according to claim 28, further comprising:
wherein said amount of pressure correlates to a predetermined speed of images displayed on the touch screen, with increased pressure relating to a faster speed, and decreased pressure to a slower speed.

31. The computer system according to claim 28, further comprising:
means for linking graphical data with text and image-based data to said report.

32. The computer system according to claim 28, further comprising:
means for forwarding said report via predetermined methods, to predetermined recipients.

33. The computer system according to claim 28, further comprising:
a camera disposed in said pen navigational device, for performing scanning functions.

34. The computer system according to claim 28, further comprising:
a wireless transmission mechanism disposed in said pen navigational device, to transmit data from said pen navigational device to said computer system.

35. A computer system for identifying and annotating a radiological image from an electronic medical record displayed on a touch screen, using a pen navigational device, comprising:
at least one memory containing at least one program comprising the steps of:
displaying a medical image on the touch screen of a computer monitor of a client computer;
receiving an instruction to link data from the electronic medical record (EMR) of a patient, which is stored in a database of one of a client computer or server computer, to the image on the touch screen;
providing a color coded system in the pen navigational device, such that the pen navigational device can utilize color coding to identify, annotate, and prioritize portions of the image on the touch screen;
wherein said color coding includes identifying different levels of clinical priority requiring action, on said image;
calculating a pressure applied by the pen navigational device on the touch screen using a pressure sensing means at the client computer, in order to determine an amount of pressure applied, said amount of pressure which indicates one of said different levels of clinical priority requiring action, an increased pressure indicating a higher level of clinical priority with a corresponding predetermined color coding, and a decreased pressure indicating a lower level of clinical priority with a different corresponding predetermined color coding;
displaying the annotated image with each of said different levels of color coding representing each of said different levels of clinical priority; and
receiving and storing said annotated image with said different levels of color coding, in said database; and
a processor which executes the program.

36. The computer system according to claim 35, further comprising:
means for performing a security protocol prior to displaying the image, to determine at least one of access and privileges related to a user.

37. The computer system according to claim 35, further comprising:
means for linking graphical data with text and image-based data to said report.

38. The computer system according to claim 35, further comprising:
means for forwarding said report to predetermined recipients via a predetermined protocol.

39. A computer-readable medium whose contents cause a computer system to identify and annotate a radiological image from an electronic medical record displayed on a touch screen using a pen navigational device, said computer system containing a program which performs the steps of:
displaying a medical image on the touch screen of a computer monitor of a client computer;
receiving an instruction to link data from the electronic medical record (EMR) of a patient, which is stored in a database of one of a client computer or server computer, to the image on the touch screen;
providing a color coded system in the pen navigational device, such that the pen navigational device can utilize color coding to annotate and prioritize portions of the image on the touch screen;
wherein said color coding includes identifying different levels of clinical priority requiring action, on said image;
calculating a pressure applied by the pen navigational device on the touch screen using a pressure sensing means at the client computer, in order to determine an amount of pressure applied, said amount of pressure which indicates one of said different levels of clinical priority requiring action, an increased pressure indicating a higher level of clinical priority with a corresponding predetermined color coding, and a decreased pressure indicating a lower level of clinical priority with a different corresponding predetermined color coding;
displaying the annotated image with each of said different levels of color coding representing each of said different levels of clinical priority; and
receiving and storing said annotated image with said different levels of color coding, in said database.

40. The computer-readable medium according to claim 39, further comprising:
performing a security protocol prior to displaying the image, to determine at least one of access and privileges related to a user.

41. The computer-readable medium according to claim 39, further comprising:
linking graphical data with text and image-based data to said report.

42. The computer-readable medium according to claim 39, further comprising:
forwarding said report to predetermined recipients via predetermined protocols.

* * * * *